(12) United States Patent
Konstantino

(10) Patent No.: US 9,180,273 B2
(45) Date of Patent: Nov. 10, 2015

(54) METHOD FOR LOADING SUBSTANCES INTO DRUG DELIVERY CATHETER

(71) Applicant: Michal Konstantino, Orinda, CA (US)

(72) Inventor: Michal Konstantino, Orinda, CA (US)

(*) Notice: Subject to any disclaimer, the term of this patent is extended or adjusted under 35 U.S.C. 154(b) by 158 days.

(21) Appl. No.: 13/667,168

(22) Filed: Nov. 2, 2012

(65) Prior Publication Data

US 2013/0302507 A1    Nov. 14, 2013

Related U.S. Application Data

(60) Division of application No. 13/162,296, filed on Jun. 16, 2011, which is a continuation of application No. PCT/US2009/068652, filed on Dec. 18, 2009.

(60) Provisional application No. 61/138,858, filed on Dec. 18, 2008.

(51) Int. Cl.
*A61M 25/00* (2006.01)
*A61M 25/10* (2013.01)

(52) U.S. Cl.
CPC ........... *A61M 25/0009* (2013.01); *A61M 25/10* (2013.01); *A61M 2025/105* (2013.01)

(58) Field of Classification Search
CPC ................... A61M 2025/105; A61M 25/0009; A61M 25/10
USPC ...................... 141/2, 114; 623/1.11; 424/423; 604/103.02
See application file for complete search history.

(56) References Cited

U.S. PATENT DOCUMENTS

| | | | |
|---|---|---|---|
| 4,927,418 A | 5/1990 | Dake et al. | |
| 5,102,401 A | 4/1992 | Lambert et al. | |
| 5,306,250 A | 4/1994 | March et al. | |
| 5,324,261 A * | 6/1994 | Amundson et al. | 604/103.02 |
| 5,370,614 A | 12/1994 | Amundson et al. | |
| 5,707,385 A | 1/1998 | Williams | |
| 7,105,013 B2 | 9/2006 | Durcan | |
| 7,396,538 B2 * | 7/2008 | Granada et al. | 424/422 |
| 8,057,813 B2 * | 11/2011 | Toner et al. | 424/422 |
| 8,109,904 B1 | 2/2012 | Papp | |
| 8,381,774 B2 * | 2/2013 | Mitchell et al. | 141/1 |
| 8,431,145 B2 * | 4/2013 | Toner et al. | 424/422 |
| 8,460,745 B2 * | 6/2013 | Mitchell et al. | 427/2.24 |
| 8,632,846 B2 * | 1/2014 | Avelar et al. | 427/2.24 |
| 8,733,408 B2 * | 5/2014 | Pacetti | 141/270 |
| 2003/0064965 A1 | 4/2003 | Richter | |
| 2005/0055014 A1 | 3/2005 | Coppeta et al. | |
| 2005/0101522 A1 | 5/2005 | Speck et al. | |
| 2005/0187602 A1 | 8/2005 | Eidenschink | |

(Continued)

OTHER PUBLICATIONS

Office action dated Jun. 7, 2013 for U.S. Appl. No. 13/162,296.

(Continued)

*Primary Examiner* — Timothy L Maust
(74) *Attorney, Agent, or Firm* — Wilson Sonsini Goodrich & Rosati

(57) ABSTRACT

Methods and apparatus for delivering a substance to a target tissue are provided which may include any number of features. One feature is storing a substance or drug in a reservoir or reservoirs over an expandable member. The expandable member can be a balloon catheter, for example. The reservoir(s) can be disposed in a Transforming Reservoirs Matrix layer disposed over the expandable member. Another feature is a mechanical activator or a plurality of mechanical activators positioned near the reservoir(s).

3 Claims, 6 Drawing Sheets

(56) References Cited

U.S. PATENT DOCUMENTS

| | | |
|---|---|---|
| 2007/0185009 A1 | 8/2007 | Unger |
| 2008/0118544 A1 | 5/2008 | Wang |
| 2008/0255510 A1 | 10/2008 | Wang |
| 2009/0227948 A1 | 9/2009 | Chen et al. |
| 2010/0076401 A1* | 3/2010 | Von Oepen et al. .......... 604/509 |
| 2012/0123388 A1 | 5/2012 | Konstantino |

OTHER PUBLICATIONS

International search report and written opinion dated Aug. 2, 2010 for PCT/US2009/068652.

Office action dated Nov. 27, 2012 for U.S. Appl. No. 13/162,296.

* cited by examiner

METHOD FOR LOADING SUBSTANCES INTO DRUG DELIVERY CATHETER

CROSS REFERENCE TO RELATED APPLICATIONS

This application is a divisional of U.S. patent application Ser. No. 13/162,296, filed Jun. 16, 2011, which is a continuation of PCT Application No. PCT/US2009/068652, filed Dec. 18, 2009, and claims the benefit under 35 U.S.C. 119 of U.S. Provisional Patent Application No. 61/138,858, filed Dec. 18, 2008, the full disclosures of which are incorporated herein by reference.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD OF THE INVENTION

The present invention relates to the field of medical devices, more specifically to devices intended to deliver active substances to body tissue.

BACKGROUND OF THE INVENTION

Local drug delivery vehicles have been in development for different applications. A particular interest of this application is local drug delivery with non-implant vehicles that can deliver a therapeutic agent, a biological agent, cell base therapy, an active agent or a substance of any kind to a desired anatomical target and release it in a relatively short engagement time of seconds to minutes, hours or in some cases days. Potential applications include treating tumors or cancer of any kind, internal or external bodily injury sites, areas of inflammations or infections, treatment of stenosis or restenosis, vulnerable plaque, ischemic or hemorrhagic stroke, promotion of wound healing and other conditions that can be treated using therapeutic or other known agents. Examples of drug delivery vehicles may be found, e.g., in U.S. Pat. No. 7,105,013; U.S. Pat. No. 5,306,250; U.S. Pat. No. 5,370,614; U.S. Pat. No. 5,324,261; U.S. Pat. No. 5,707,385; US Patent Appl. Publ. No. 2005/0101522; US Patent Appl. Publ. No. 2003/0064965; US Patent Appl. Publ. No. 2008/0118544; and US Patent Appl. Publ. No. 2008/0255510.

One particular application is drug delivery to body lumens using devices such as drug coated balloons (DEB). Drug coated balloons release drug to luminal walls through surface contact and diffusion. The drug is typically utilized to minimize inflammatory response during healing and improve long term patency of the lumen. In other cases therapeutic agents include substances for accelerated or enhanced healing and of the luminal wall after balloon angioplasty.

Those devices suffer from multiple limitations that hinder their effectiveness. One of the key issues is binding the drug to the balloon surface in a way that will allow the drug to release at the desired target. Typically the coatings involve additives or binders to allow the drug to bind to the surface. One example is contrast agents previously used as an additive to Paclitaxel in coated balloon application. Another example is polymeric additive such as hydrogels that react to water based environment. Dip coating, spray coating and other methods are used to attach combinations of binders or additives and drugs such as paclitaxel, Rapamycin or others to the polymeric surface of the balloon. Those formulations of drugs and additives add complexity to device and may affect the absorbency and thereby potency of the drug. In addition the device releases not just the drug but also the additive that may interfere with the healing process and affect the long term results of the treatment.

Another related limitation is that some of the drug coated on the balloon washes out during catheter delivery to the target location (literature reports include numbers of up to 80%). Delivery times vary significantly from less than 30 seconds to sometimes up to 10 minutes depending on the location of the target lesion and on the tortuosity of the anatomical pathway leading to the target. Therefore the amount of drug remaining on the coated balloon varies significantly, and the amount of drug released to the lesion cannot be controlled properly.

Attempts have been made to resolve this issue by developing new binders, adding erodible protective layers, using protective sheaths that may or may not include perforations and hiding the drug within the balloon folds. New binders and any new entity used in the circulatory system carry a risk of adverse biological effects and impaired release kinetic. Erodible protective layers further complicate the coating process and may impair the controlled release by shortening drug diffusion time (since the protective layer has to erode first) and adding another loosely controlled time variable to the drug/tissue contact time. Protective sheathes of any kind cover the drug layer, limit diffusion time and typically require the drug to be mixed with other additive that can flow through the perforated sheath. All those methods shorten the drug diffusion time, limit the ability to control the release kinetic and by that hinder the safety and effectiveness of the therapy.

Another limitation of these devices is in cases of therapeutic substances that are very active and need to be isolated until they reach the target site—such as biological sealants and fibrin sealants that may start oxidation or curing processes immediately upon contact with body fluid. Therefore these substances should be isolated throughout the delivery, regardless of length or tortousity, until the moment they reach the target site where they are activated/released.

Another limitation of drug delivery vehicles such as coated balloons is the dependence on diffusion alone to release the drug to the target during very short contact times (typically in the order of seconds or minutes). Diffusion is highly dependent on the topology and pathology of the lesion. For example, if the lesion is calcified the calcium may act as a barrier to drug diffusion and not enough substance will diffuse to the lesion.

For all those reasons there is still a need to invent and develop new vehicles for drug delivery to luminal walls and other locations in the body that will maximize the drug/tissue interaction time, minimize the need for new formulations and additives, and allow for a controlled and effective release of drug and other substances to target locations.

SUMMARY OF THE INVENTION

In one embodiment, a substance delivery apparatus is provided comprising a catheter shaft, an expandable member disposed on the catheter shaft, an expandable shell disposed on the expandable member, the expandable shell comprising a reservoir containing a substance, and a mechanical activator positioned near the reservoir, the mechanical activator being configured to apply localized mechanical force to the reservoir upon expansion of the expandable member to release the substance from the reservoir.

In some embodiments, the expandable member is an expandable balloon. In other embodiments, the expandable member is an expandable cage.

In some embodiments, the mechanical activator is disposed on the expandable member. In other embodiments, the mechanical activator is disposed between the expandable member and the expandable shell. In yet other embodiments, the mechanical activator is disposed within the reservoir.

In one embodiment, the expandable shell comprises a plurality of reservoirs each containing a substance, the apparatus further comprising a plurality of mechanical activators configured to apply localized mechanical force to the reservoirs upon expansion of the expandable member to release the substances from the reservoirs. In some embodiments, each mechanical activator corresponds to a position of each reservoir.

In some embodiments, the substance is a drug.

In some embodiments the substance is a surgical sealant or alike

In one embodiment, the reservoir is configured to retain the substance when the expandable shell is in a closed configuration and to deliver the substance when the expandable shell is in an expanded configuration.

Yet another embodiment provides a substance delivery apparatus, comprising a catheter shaft, an expandable member disposed on the catheter shaft, a reservoir disposed over the expandable member, the reservoir containing a substance, and a mechanical activator positioned near the reservoir, the mechanical activator being configured to apply localized mechanical force to the reservoir upon expansion of the expandable member to release the substance from the reservoir.

In some embodiments, the expandable member is an expandable balloon. In other embodiments, the expandable member is an expandable cage.

In one embodiment, the mechanical activator is disposed within the reservoir. In another embodiment, the mechanical activator is positioned to correspond to the location of the reservoir.

In some embodiments, the substance is a drug.

In another embodiment, the substance is a drug, the reservoir being configured to retain the drug when the expandable member is in a closed configuration and to deliver the drug when the expandable member is in an expanded configuration.

A method of treating a target tissue is provided, comprising inserting a drug delivery apparatus containing a drug into a body lumen, positioning the drug delivery apparatus at the target tissue, expanding an expandable member of the drug delivery apparatus to apply mechanical force from a mechanical activator to a reservoir, and delivering the drug from the reservoir to the target tissue.

In some embodiments, the expandable member is a balloon. In other embodiments, the expandable member is an expandable cage.

The method can further comprise the step of storing the drug in the reservoir before inserting the drug delivery apparatus into the body lumen.

A method of loading a therapeutic substance into a drug delivery catheter is provided, comprising inflating a balloon to a pressure lower than its nominal pressure, thereby partially expanding a reservoir disposed on the balloon, loading a drug on the balloon and into the reservoir, and deflating the balloon to a relaxed configuration.

DETAILED DESCRIPTION OF THE INVENTION

Figure 1A:
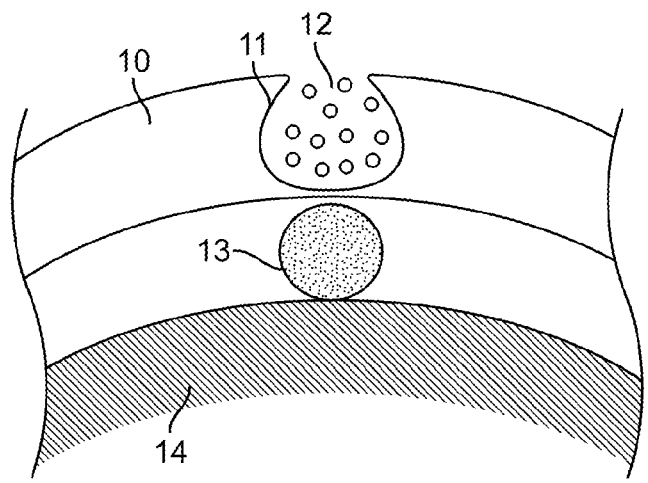
FIGS. 1A, 1B and 1C are schematic illustrations of the TRM structure with granular mechanical activators in accordance with an embodiment of the invention.

Embodiments of the present invention relate to a device for storage and transfer of therapeutic agents into body tissue and in particular into luminal walls. The invention will also find use in treating other body lumens, such as vein and synthetic grafts, as well as lumens of the respiratory, urinary, reproductive and digestive systems, and the like, for other conditions such as erectile dysfunction, ischemic and hemorrhagic stroke, lesions, tumors or some types of cancer or other disorders that may benefit from local delivery of therapeutic substance.

The present invention provides method and apparatus for rapid delivery of active substances to body tissue through utilization of transforming reservoirs coupled with mechanical activation capable of changing the reservoirs' form and actively releasing or spraying drug upon activation. The invention is directed to providing a matrix (matrix also means membrane, sheath, shell, layer or alike and can be porous or non-porous) containing multiform reservoirs for drug delivery into body lumens capable of securely transporting and upon activation actively releasing, ejecting, embedding or spraying substances and in particular therapeutic agents. The matrix does not have to be tubular and can be of different shapes, materials and dimensions. The activatable reservoir matrix is referred to as the Transforming Reservoirs Matrix (TRM) herein.

In one embodiment, the reservoirs can be activated by applying force or stress via mechanical activators on the TRM to release, push and/or embed the therapeutic agent into the target lesion. Alternatively, the TRM can transfer the therapeutic agent into target lesion or other tissue by radiation, liquid contact, chemical interactions, sound or ultrasound waves, photons, electrically, magnetically, pressure, interaction with other materials or other methods known to produce or transfer energy or induce changes. In some embodiments, activation of the reservoirs pushes or induces the drug or other agent out of the reservoir and increases the local pressure of drug loaded areas in the membrane thereby enhancing diffusion by inducing additional local mechanical stress. The drug or other agent can be stored in a powder form or any other form and does not have to include additives or binders since it does not necessarily bound to the matrix but is physically stored within a reservoir.

The reservoirs protect the drug or other agent from being washed away during catheter delivery to the target location. It also protects the drug/substance from having contact with body fluids and oxygen or light in some agents that require activation for therapeutic effectiveness. Further protection can be achieved by adding cap to seal the content of the reservoir (for example polymer cap). During activation, the reservoirs change shape and transform to push the agent outside. This action leads to enhanced drug/tissue transport properties. For example, in some embodiments the matrix layer is thinning while the stored drug is not, so the drug protrudes out to be embedded in the lesion. Furthermore, in some embodiments mechanical activators create protrusions to increase drug tissue surface contact and better embed the drug within tissue by applying localized force. This action provides stress/mechanical induced transport of drug to the lesion or desired tissue. The reservoirs can be designed in such a way that upon activation they will push the drug out and add a mechanical component to the diffusion profile.

In some embodiments, the mechanical activators are physical protrusions/bulges located under, on or within the TRM. These activators apply mechanical force/pressure on the drug reservoir to induce drug release. Their rough surface and topography create a larger surface area increasing contact between the therapeutic agent and target lesion/tissue. These activators serve to further push drug into the tissue thus promising better drug retention/uptake.

The mechanical activators can be in the form of spikes, spheres, granules, longitudinal ridges or a skeleton—any physical protrusion that creates mechanical pressure to help induce the therapeutic agent's release. They can be located on a separate layer under the TRM, or within the TRM. They can be a part of the delivery system. These protrusions can be randomly scattered thus statistically improving the drug release mechanism and increasing drug tissue contact. They can also be specifically designed and placed on the delivery system.

The TRM can be double layer, multi layer or made of one layer. They can be in an expandable layer or shell on surrounding the balloon or can be incorporated into the balloon itself. The transforming reservoirs can be drilled, etched, laser formed, printed, pressed or made in other conventional ways using one layer matrix or combination of multiple layers to achieve the desired shape.

In one embodiment the TRM is made of elastic material and activated by expansion and mechanical pressure. In this example the TRM can be made of materials such as Nylon, Pebax, Polyurethane or other materials commonly used for vascular devices (such as balloon catheters). The TRM has multiple states of expansion between its collapsed and expanded states. In this embodiment, the drug or therapeutic agent is loaded in the intermediate state, the matrix is then relaxed to its collapsed state and the reservoirs are closed on the drug. Once the matrix is expanded to the expanded state (in this example expanded past the intermediate state) the reservoirs are fully opened and release the drug to the surrounding tissue.

The above elastic TRM can be used to release an anti-inflammatory drug or other desired substance formulation to stenosed blood vessels. In one example, three states will be used: collapsed, expanded and an intermediate state in between. The reservoirs can be formed in any of the states, such as the expanded state and or an intermediate state. The therapeutic agent is loaded to the TRM in one of the expanded or intermediate states. Once the TRM is collapsed, the reservoirs are closed on the drug, and the drug can be stored and delivered to the target artery safely. The TRM is then activated to an expanded state by expansion of an underlining shell/layer such as a balloon or an expandable cage. At this point the drug is released out of the fully open reservoirs with the aid of local mechanical activators placed in proximity to the reservoirs. The mechanical activators apply local force to reshape the reservoirs during expansion. The drug or therapeutic agent can further be embedded into the vessel wall by the force of the expansion and local mechanical force applied by the protrusions caused by mechanical activators.

In one embodiment a balloon can be coated and reservoirs formed in that outer layer to create an expandable TRM shell. The therapeutic agent/substance is then loaded in the intermediate stage. Following this the TRM layer is relaxed into its closed state which is best for drug retention. Upon inflation of the balloon the TRM layer expands and allows the flow of drug to the desired target. The inflation process creates mechanical pressure thus pushing the drug out—this can be done with or without the mechanical activators. Furthermore the expansion of the TRM makes that layer thin which further pushes the drug out.

In one embodiment only two states of expansion exist: collapsed and expanded. The desired substance formulation can be loaded in each one of the states. For example the drug can be injected into the reservoir while in the collapsed state or applied by common means of coating such as spraying, dipping or spot coating at any selected state of expansion state.

TRM can be formed from any material or layer that can change its shape between storage and catheter advancement phase (typically collapsed) to the operational phase or drug delivery phase. In between those 2 stages an additional intermediate stage can be identified and utilized as the drug loading stage. In the case of drug eluting balloons the delivery phase will be the deployment stage in which the balloon or the carrying shell is expanded.

Materials that can be used for TRM include all known balloon catheters material such as Pebax, polyurethane, Nylon, Silicon, polyethylene, PVA and virtually all polymers that can be formed into a membrane or shell form. The materials may consist of resorbable polymers and/or hydrogels such as PEG, PEO, PLG and PLA among others. Conductive polymers can also be used with TRM triggering by application of electrical current. Mechanical activators can be fabricated using the above materials and known methods affecting polymer topography and surface roughness such as plasma etching, molding, heat processing, chemical modifications, laser processing or other methods known in the arts. The activators can also be fabricated from other materials such as ceramic materials, oxides, composite materials, carbon particles, metals, certain adhesives such as acrylic based adhesives, glass base materials and others. Typically the activators material will be harder than the TRM base material however the same material or type of materials may be used for both.

Metallic or oxide base layers can be used as well. Metallic shell can be triggered to activate the TRM. One example is triggering by applying heat to Nickel Titanium shells with shape memory characteristics. Application of electrical current can also be used to trigger TRM release and enhance drug diffusion. Shape memory polymers may be an excellent choice for TRM having unique characteristics of retaining a predetermined shape while being bio-compatible and have elastic and plastic properties of polymers.

In another embodiment the TRM is in a form of a mesh with a webbed film of polymer and therapeutic agent. Mechanical activators are located under the meshed film. Upon activation the mechanical activators press against the film causing mechanical induced transport of the drug out of the film into the tissue.

In another embodiment drug (or substance) delivery apparatus is used to deliver substance that promotes and enhance wound healing both in cases of external or internal uses. For example the apparatus is loaded with fibrin based sealant and delivered to a site of an arterial dissection or vascular injury, there the expandable member or the TRM expands and the substance is released using pressure and mechanical force, when the drug delivery apparatus is removed the dissection is at least partially sealed and regular blood flow resumes. Another example is promoting wound healing using the TRM in areas such as minimizing post surgery bleeding in the adenoids (post T&A surgery), colon perforations or vascular surgery. Additional novel application is sealing valve leaks post valve surgery (such as aortic valve) or transcatheter/ transepical valve replacement using stent valve or similar devices. Application of sealants can be done using TRM or otherwise using an expandable member or expandable shell with reservoirs.

The transforming reservoirs, the mechanical activators and methods of use as described in the present invention can be utilized to deliver a wide variety of therapeutic, cellular and pharmaceutical agents, referred to collectively herein as active substances or drugs, particularly those suitable for treating vascular and other luminal conditions, including but not limited to the following: (1) antiproliferative and antimitotic agents such as natural products such as vinca alkaloids (i.e. vinblastine, vincristine, and vinorelbine), paclitaxel, epidipodophyllotoxins (i.e. etoposide, teniposide), antibiotics (dactinomycin, actinomycin D, daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); (2) antiplatelet agents such as G(GP) II.b/III.a inhibitors and vitronectin receptor antagonists; (3) alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); (4) antiproliferative and antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); (5) platinum coordination complexes such as cisplatin, carboplatin, procarbazine, hydroxyurea, mitotane, and aminoglutethimide; (6) hormones (e.g. estrogen); (7) anticoagulants (heparin, synthetic heparin salts and other inhibitors of thrombin); (8) fibrinolytic agents (such as tissue plasminogen activator, streptokinase and urokinase), aspirin, dipyridamole, ticlopidine, clopidogrel, abciximab; (9) antimigratory agents; (10) antisecretory agents (breveldin); (11) anti-inflammatory agents, such as adrenocortical steroids (cortisol, cortisone, fludrocortisone, prednisone, prednisolone, 6.alpha.-methylprednisolone, triamcinolone, betamethasone, and dexamethasone), non-steroidal agents (salicylic acid derivatives i.e. aspirin; para-aminophenol derivatives i.e. acetaminophen; (12) indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); (13) immunosuppressive agents such as cyclosporine, tacrolimus (FK-506), sirolimus (rapamycin), azathioprine, mycophenolate, mofetil; (14) angiogenic agents such as vascular endothelial growth factor (VEGF), fibroblast growth factor (FGF); (15) angiotensin receptor blockers; (16) nitric oxide donors; (17) anti-sense oligionucleotides and combinations thereof; (18) cell cycle inhibitors, mTOR inhibitors, and growth factor receptor signal transduction kinase inhibitors; (19) retenoids; (20) cyclin/ CDK inhibitors; (21) HMG co-enzyme reductase inhibitors (statins); and (22) protease inhibitors. (23) surgical and biological sealants such as fibrin sealants (for example fibrinogen, thrombin), glutaraldehyde glues, collagen based sealants, cyanoacrylates and hydrogel based glues.

Reference is now made to FIG. 1A which is a schematic illustration of a drug delivery apparatus including a TRM 10 (also referred to herein as an expandable shell). The TRM 10 includes at least one reservoir 11 shown in FIG. 1A in a closed state (also referred to as a constrained closed configuration), which contains or retains a therapeutic substance or drug 12. The therapeutic agent can be a drug, drug formulation, combination of drug and additives such as polymer or micro or nano spheres, cellular agents or other desirable combination of substances. The TRM 10 can be disposed on a balloon or expandable member 14 of choice (which can be a balloon, expandable cage or other structure configured to increase its effective diameter in response to a trigger). Mechanical activators 13 can be disposed between the TRM 10 and the expandable member 14. The mechanical activators can be positioned so as to correspond to the reservoirs on the TRM. As is customary in the field of balloon catheters, the balloon or expandable member 14 can be mounted on a catheter shaft, and typically on a distal end of the catheter shaft (catheter shaft not shown in FIGS. 1A-1C for ease of description).

The mechanical activators 13 can press against the TRM 10 and the reservoirs 11 and apply localized mechanical force to the TRM and reservoirs upon expansion of the expandable shell 14 from a constrained, closed configuration, to an expanded drug delivery configuration. The mechanical activators can further deform the reservoirs, and in some cases invert the shape of the reservoirs upon expansion of the expandable shell (as shown in FIG. 1C). The expansion can mechanically release or spray the therapeutic substance 12 out of the TRM and help embed the substance into the desired targeted tissue or lesion.

Figure 1B:
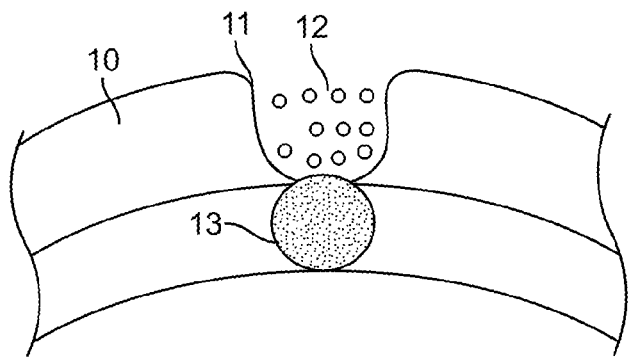
Figure 1C:
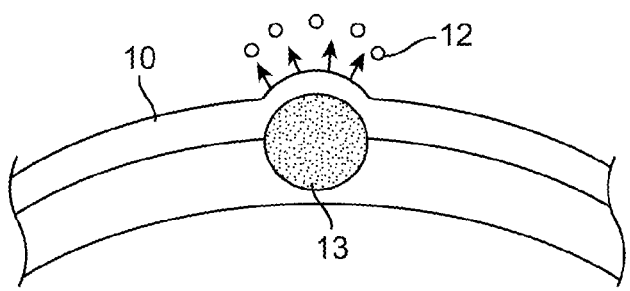

FIG. 1B demonstrates an intermediate expansion state (also referred to as an intermediate configuration) of the TRM that may be used in one embodiment to load substance into the reservoirs. For example, the expandable member or balloon can be partially inflated to a pressure lower than its nominal pressure, causing the reservoirs 11 to partially open or expand. The therapeutic substance 12 can then be loaded onto the balloon and into the reservoirs, and the expandable member or balloon can be deflated to its relaxed or deflated configuration, causing the TRM and reservoirs to assume a constrained, closed configuration, thereby depositing the drug into the reservoirs.

FIG. 1C shows the expanded state (also referred to as an expanded drug delivery configuration) of the TRM and the full impact of the mechanical activators on the shape of the reservoir, thereby opening the reservoirs and releasing the content of the reservoir into the targeted tissue, pushing the substance out of the reservoir and into the tissue and applying mechanical force to embed the substance into the tissue, preventing it from being washed into the blood stream, and enhancing the release kinetic of the substance beyond simple diffusion by adding mechanical components (stress induced diffusion).

The combination of the mechanical activators with the TRM also increases the total surface contact area and in particular increases the local surface contact area beyond the cylindrical surface area of the carrying balloon by adding a three dimensional aspect to the surface (for example in the case of granular activator the TRM surface will include circular protrusions).

Figure 2:
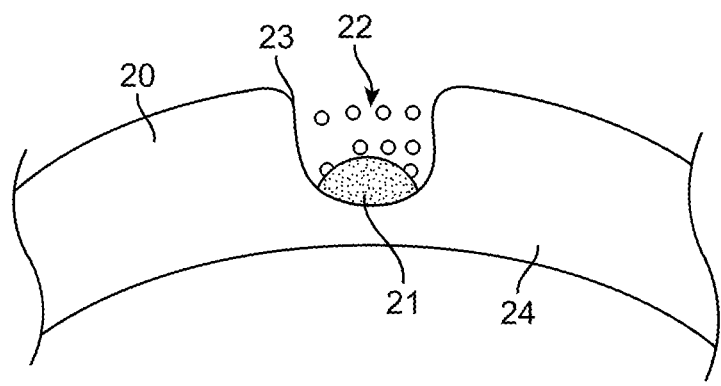
FIG. 2 is a schematic illustration of an exemplary reservoir with an inner reservoir mechanical activator.

In reference to FIG. 2, mechanical activator 21 is located within reservoir 23 under the therapeutic substance 22. When pressure is applied to the TRM 20 and mechanical activator by expandable member 24, the mechanical activator assists delivery of the substance 22 by releasing, pushing and embedding the therapeutic agent into the target area. The fabrication of the TRM includes inserting the mechanical activator into the bottom portion of the reservoir and securing it in place prior to loading the therapeutic substance. This can be achieved by known methods such as polymerization, adhesion and curing. The mechanical activator can be made of any suitable material that is stable and tough such as PE or PMMA. It can also be made of biodegradable polymers in the event of release from the reservoir.

Figure 3A:
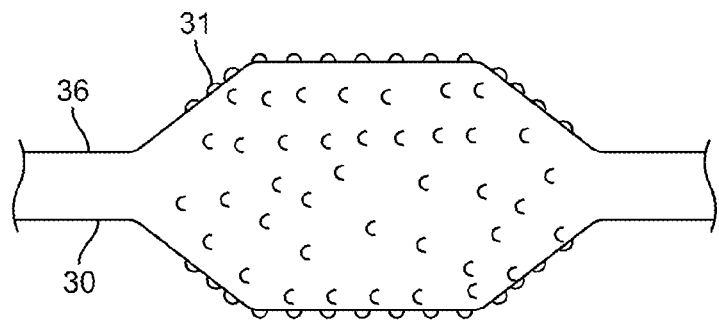
FIGS. 3A-C are a schematic illustration of an expanded angioplasty balloon with granular or spherical roughening carrying a TRM structure in accordance with embodiments of the invention.
Figure 3B:
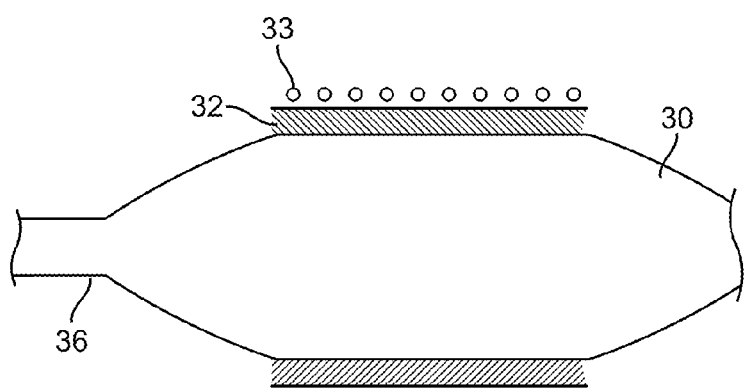
Figure 3C:
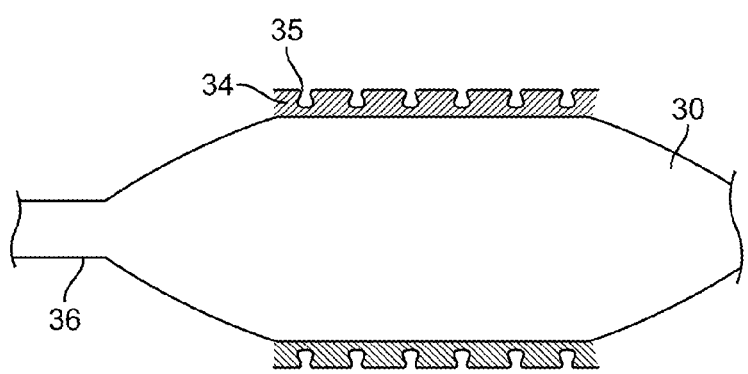

In another embodiment referring to FIG. 3A the mechanical activators 31 are granules on the surface of a carrying balloon 30. The carrying balloon 30 can be disposed near a distal end of catheter shaft 36, for example. These granules 31 can be randomly scattered on the balloon surface with no specific regard to the location of the reservoirs on the TRM. In this case they statistically improve the release process from the TRM by applying mechanical pressure on the TRM and increasing the contact surface between the TRM and the tissue. These granules can also be placed on the balloon or in a separate layer in a methodical order or shape (ridges/grid) to achieve maximal efficiency in releasing drug from TRM and penetrating the tissue. These granules can be on the surface of the balloon or in a separate layer coating the balloon. FIGS. 3B and 3C give further examples of the TRM layer (32 in FIGS. 3B and 34 in FIG. 3C). In FIG. 3B the therapeutic agent 33 is coated on top of the TRM, and in FIG. 3C it is located within reservoirs 35.

Figure 4A:
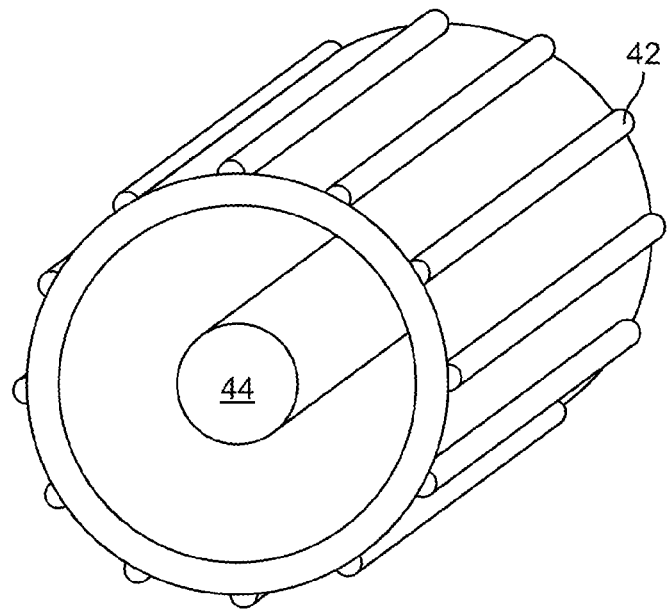
FIGS. 4A and 4B are a schematic illustration of an exemplary circular TRM structure with ridges.
Figure 4B:
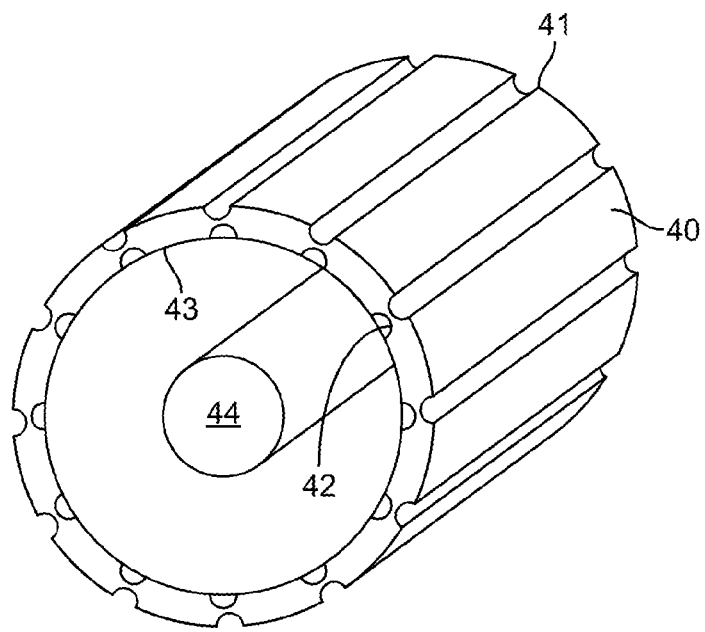

In the embodiment of FIG. 4A, the mechanical activators are located in a separate layer as longitudinal ridges protruding from the surface. In the case of balloon angioplasty, shown in FIG. 4B, this layer is placed on top of the balloon 43 and under the TRM layer 40. In addition, the transforming reservoirs 41 are longitudinal crevices, dents or depressions on the surface of the TRM. When balloon 43 is inflated, the mechanical activators press against the transforming reservoirs, causing them to open and push the therapeutic substance from within the reservoirs onto the vessel wall. The mechanical activators not only mechanically force the drug out but they serve to insert the drug deep into the tissue and increase the surface contact between the balloon and the surrounding tissue. This is similar to the process described in FIGS. 1A-1C. FIGS. 4A-4B also show a cross sectional view of catheter shaft 44. It should be understood that the balloon and TRM layer can be disposed anywhere on the catheter shaft, but in some embodiments they are disposed near a distal end of the catheter shaft.

Figure 5A:
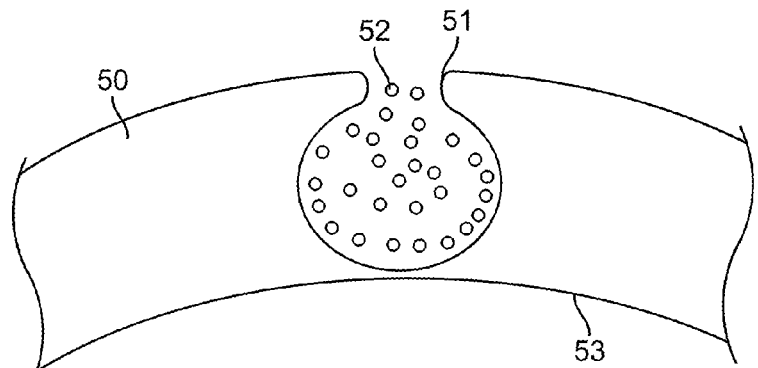
FIGS. 5A-C illustrate unique reservoir formation structure with three states of expansion.
Figure 5B:
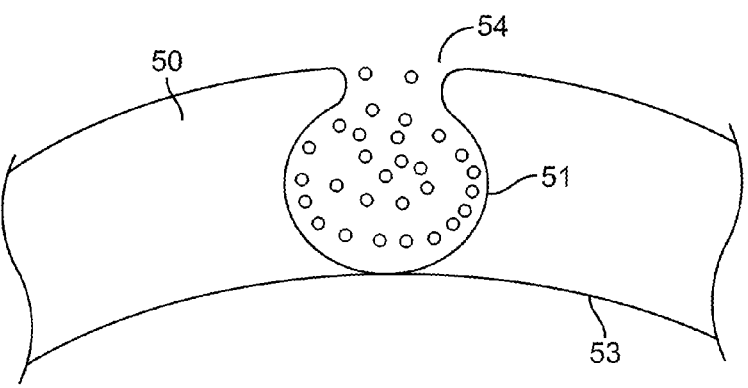
Figure 5C:
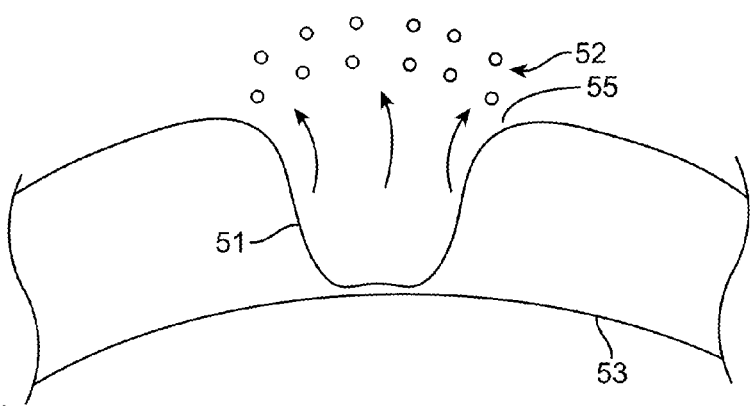

Reference is now made to FIG. 5A which is a schematic illustration of a TRM 50. In this embodiment, the TRM can be placed on a balloon 53 forming an expandable shell of reservoirs or a porous layer. TRM 50 includes at least one reservoir described at a closed state 51, which contains a therapeutic substance 52. In this embodiment the transforming reservoirs allow drug retention in the closed state. In FIG. 5B, the TRM is in an intermediate state 54, which can be utilized to load therapeutic substance. FIG. 5C illustrates the TRM in an open/releasing state 55, which allows the reservoir to release or spray the drug to a target lesion. The special shape of the reservoir allows maximum efficiency in each state—drug retention in the closed state (FIG. 5A) during storage and during delivery to the target area, drug loading in the intermediate state (FIG. 5B) (this state is also effective to insert a mechanical activator as described in FIG. 2), and stress/mechanical induced release in the open state (FIG. 5C).

A method drug delivery can be as follows, utilizing any of the drug delivery apparatus described above: the balloon of the drug delivery apparatus can be slightly inflated to allow drug loading into the reservoirs, as shown in the intermediate stage (FIG. 5B). Then the balloon can be relaxed and stored, the drug is stored in the closed reservoir, (FIG. 5A) where it is best protected during storage and delivery to target site. The drug delivery apparatus can be inserted into a human body lumen and navigated to a target tissue site within the body. When the expandable balloon member of the apparatus is positioned near the target site, the expandable member can be inflated or expanded. Upon expansion of the expandable member, the reservoirs can be opened, causing the drug to be released to the target tissue (FIG. 5C). This is achieved through stress and mechanical force. In some embodiments, mechanical activators apply localized mechanical force to the reservoirs upon expansion of the expandable member. The mechanical activators can further deform the reservoirs, and in some cases invert the shape of the reservoirs upon expansion of the expandable member.

Figure 6:
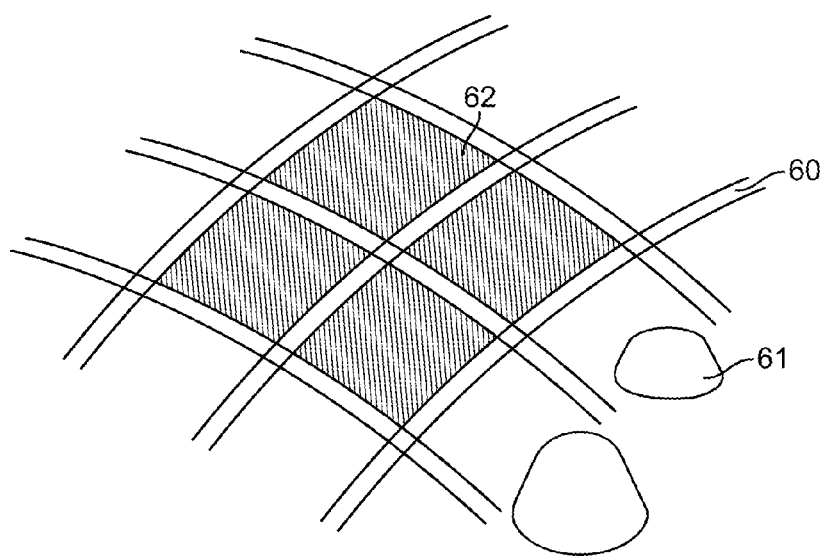
FIG. 6 is a schematic illustration of an exemplary mesh with webbing of drug/polymer film and mechanical activators.
Figure 7:
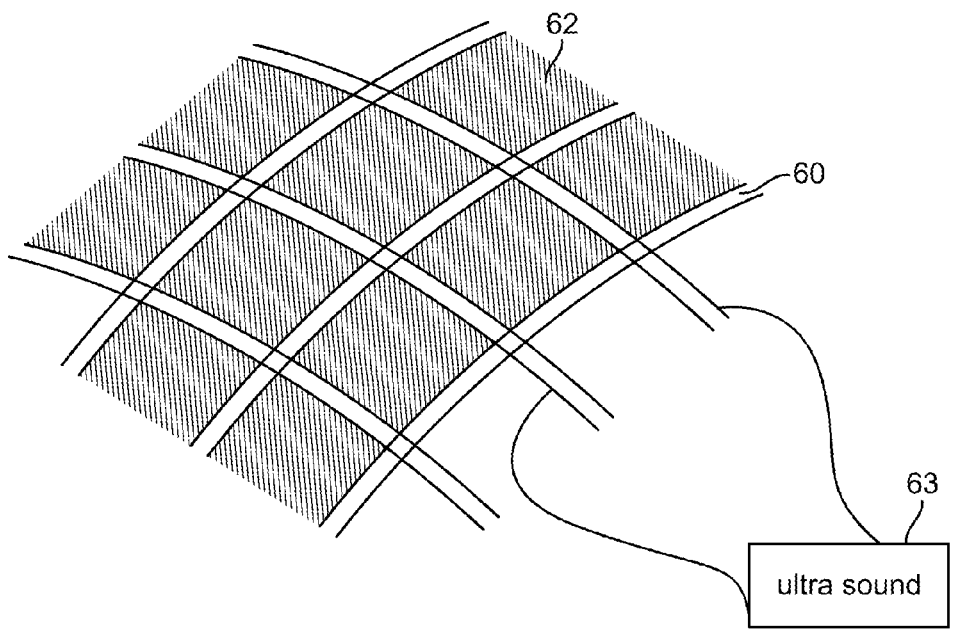
FIG. 7 is a schematic illustration of an exemplary mesh with webbing of drug/polymer film and ultrasound activators.

FIGS. 6 and 7 illustrate a polymeric mesh/net 60 with a therapeutic agent film webbing 62. In this embodiment the TRM can be activated by mechanical activators 61 or, alternatively, can be activated by ultrasound 63. However, any activation method such as electrical current or magnetic field thermal activation that will cause reservoir transformation and drug release can apply.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method of loading a therapeutic substance into a drug delivery catheter, comprising:
    inflating a balloon to a pressure selected to partially expand a plurality of reservoirs having open, intermediate, and closed states disposed in a transforming matrix on an outside surface of the balloon, wherein the reservoirs are partially expanded to their intermediate states;
    loading a drug into the plurality of reservoirs on the balloon while the reservoirs are in their intermediate states; and
    deflating the balloon to a relaxed configuration.

2. A method as in claim 1, wherein deflating the balloon returns the reservoirs to their closed configuration.

3. A method as in claim 1, wherein the drug is loaded by spraying, dipping, or spot coating.

* * * * *